(12) United States Patent
Cox

(10) Patent No.: US 9,551,614 B2
(45) Date of Patent: Jan. 24, 2017

(54) DEVICES, METHODS, AND SYSTEMS FOR CAVITY-ENHANCED SPECTROSCOPY

(71) Applicant: Honeywell International Inc., Morristown, NJ (US)

(72) Inventor: James Allen Cox, New Brighton, MN (US)

(73) Assignee: Honeywell International Inc., Morris Plains, NJ (US)

( * ) Notice: Subject to any disclaimer, the term of this patent is extended or adjusted under 35 U.S.C. 154(b) by 96 days.

(21) Appl. No.: 14/577,130

(22) Filed: Dec. 19, 2014

(65) Prior Publication Data

US 2015/0377704 A1  Dec. 31, 2015

Related U.S. Application Data

(60) Provisional application No. 62/019,147, filed on Jun. 30, 2014.

(51) Int. Cl.
| | |
|---|---|
| *G01J 3/28* | (2006.01) |
| *G01J 3/10* | (2006.01) |
| *G01J 3/32* | (2006.01) |
| *G01J 3/42* | (2006.01) |
| *G01N 21/3504* | (2014.01) |
| *G01N 21/03* | (2006.01) |
| *G01N 21/359* | (2014.01) |
| *G01N 21/39* | (2006.01) |

(52) U.S. Cl.
CPC ............... *G01J 3/10* (2013.01); *G01J 3/108* (2013.01); *G01J 3/32* (2013.01); *G01J 3/42* (2013.01); *G01N 21/031* (2013.01); *G01N 21/3504* (2013.01); *G01N 21/359* (2013.01); *G01J 2003/423* (2013.01); *G01N 2021/391* (2013.01)

(58) Field of Classification Search
CPC .................. G01J 3/28; G01J 3/02; G01J 3/10; G01J 3/208
USPC ................................................ 356/300–344
See application file for complete search history.

(56) References Cited

U.S. PATENT DOCUMENTS

| | | | |
|---|---|---|---|
| 6,201,638 B1 * | 3/2001 | Hall ..................... | G02F 1/395 359/346 |
| 8,120,773 B2 * | 2/2012 | Gohle ................... | G01J 3/10 356/319 |

* cited by examiner

*Primary Examiner* — Abdullahi Nur
(74) *Attorney, Agent, or Firm* — Brooks, Cameron & Huebsch, PLLC

(57) ABSTRACT

Devices, methods, and systems for cavity-enhanced spectroscopy are described herein. One system includes an optical frequency comb (OFC) coupled to a laser source, and a cavity coupled to the OFC comprising a number of mirrors, wherein at least one of the number of mirrors is coupled to a piezo-transducer configured to alter a position of the at least one of the number of mirrors.

20 Claims, 3 Drawing Sheets

DEVICES, METHODS, AND SYSTEMS FOR CAVITY-ENHANCED SPECTROSCOPY

TECHNICAL FIELD

The present disclosure relates to devices, methods, and systems for cavity-enhanced spectroscopy.

BACKGROUND

A spectrometer can be utilized to identify an unknown substance by determining the absorption spectrum (e.g., spectral content) of the substance. For example, previous spectrometry may use broadband blackbody light sources (e.g., having a temperature of approximately 1500 Kelvins) and infrared Fourier transform spectroscopy to determine the absorption spectrum of an unknown substance.

The blackbody light sources of such previous spectrometers, however, may have a low radiation, which can limit the performance of the spectrometer. For example, previous spectrometers may not be able to effectively determine the absorption spectrum of an unknown substance, and accordingly may not be able to accurately identify the unknown substance, as a result of the low radiation of their blackbody light sources.

DETAILED DESCRIPTION

Figure 1:
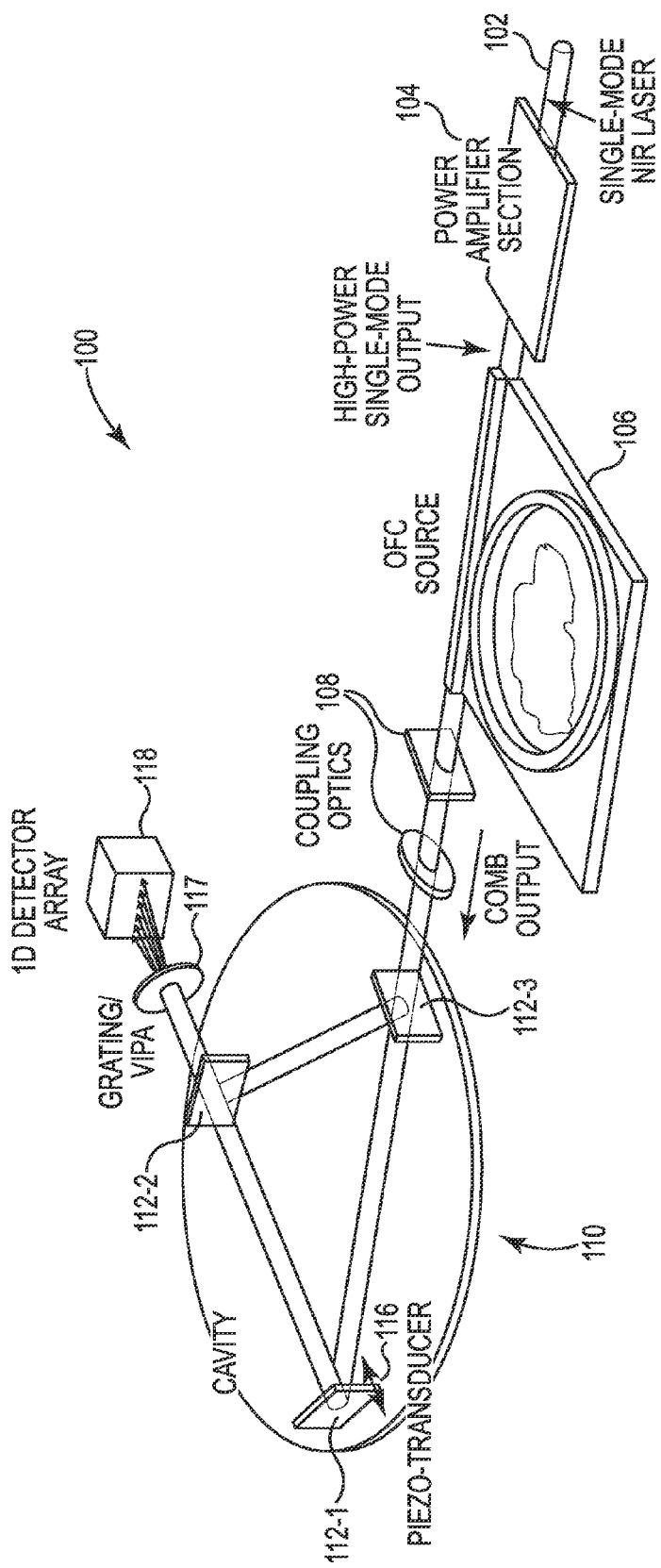
FIG. 1 is an example of a system for cavity-enhanced spectroscopy according to one or more embodiments of the present disclosure.

Devices, methods, and systems for cavity-enhanced spectroscopy are described herein. For example, one or more embodiments include a system that includes an optical frequency comb (OFC) coupled to a laser source, and a cavity coupled to the OFC comprising a number of mirrors, wherein at least one of the number of mirrors is coupled to a piezo-transducer configured to alter a position of the at least one of the number of mirrors.

Devices, methods, and systems for cavity-enhanced spectroscopy can be utilized to detect a number of gasses simultaneously with a 3-sigma limit of detection (LOD) (e.g., 1 parts per billion (ppb)) for both narrow-line absorbing gas and broad-band absorbing gas. For purposes of performance comparison, cavity-enhanced spectroscopy as described herein can have a one second integration time. The cavity-enhanced spectroscopy can provide the limit of detection within a relatively smaller volume and relatively lower power compared to previous systems and methods of spectroscopy.

Cavity-enhanced spectroscopy can utilize an OFC coupled to a laser source with an output of the OFC coupled to a cavity. The cavity can comprise a number of mirrors (e.g., 3 mirrors, etc.) to reflect the light output from the OFC between the number of mirrors. Reflecting the light output from the OFC between the number of mirrors can extend an effective path (e.g., distance traveled by the output light of the OFC) of the light output from the OFC beyond an actual path length (e.g., physical distance between mirrors) between the number of mirrors. As used herein, the effective path is a distance traveled by the light output from the OFC. For example, the effective path of a cavity-enhanced spectroscopy can be approximately 2 kilometers to 3 kilometers. That is, the light travels between the mirrors a plurality of times to reach a distance of approximately 2 kilometers to 3 kilometers. As used herein, the actual path length is a measured distance between the number of mirrors within the cavity. For example, the actual path length can be approximately 6 centimeters. That is, the distance between a first mirror, to a second mirror, and to a third mirror is approximately 6 centimeters.

The number of mirrors can comprise low loss mirrors with a relatively low loss over a relatively wide spectral band. That is, the number of mirrors can comprise mirrors that do not absorb light over a relatively wide spectral band (e.g., half octave, 500 nanometers (nm) in the near infrared (NIR), etc.). In some embodiments, at least one of the number of mirrors is coupled to a piezo-transducer that is configured to alter a position of the mirror. A piezo-transducer can be utilized to make precise and/or small distance alterations to the position of the mirror utilizing a relatively low amount of power.

Altering the position of at least one of the number of mirrors can bring each comb line from the output light of the OFC into a resonance with the cavity. For example, the output light from the OFC can comprise a plurality of comb lines at a number of different wavelengths. In this example, each of the plurality of comb lines may not lie exactly on a cavity resonance. In this example, the piezo-transducer can alter a position of at least one of the number of mirrors to bring each of the plurality of comb lines into resonance with the cavity to increase or decrease an effective distance of the output light from the OFC to generate a plurality of comb lines in the near infrared region, and allow each of the plurality of comb lines to interact with a gas within the cavity. Embodiments described herein include examples of generating comb lines in the near infrared (NIR) region, however the same concepts and examples can also be applicable across the spectrum the ultraviolet (UV) region to the far infrared region.

In the following detailed description, reference is made to the accompanying drawings that form a part hereof. The drawings show by way of illustration how one or more embodiments of the disclosure may be practiced.

These embodiments are described in sufficient detail to enable those of ordinary skill in the art to practice one or more embodiments of this disclosure. It is to be understood that other embodiments may be utilized and that process changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense.

The figures herein follow a numbering convention in which the first digit or digits correspond to the drawing figure number and the remaining digits identify an element or component in the drawing. Similar elements or components between different figures may be identified by the use of similar digits.

As used herein, "a" or "a number of" something can refer to one or more such things. For example, "a number of widgets" can refer to one or more widgets. Additionally, the designator "N", as used herein, particularly with respect to reference numerals in the drawings, indicates that a number of the particular feature so designated can be included with a number of embodiments of the present disclosure.

FIG. 1 is an example of a system 100 for cavity-enhanced spectroscopy according to one or more embodiments of the present disclosure. The system 100 can be utilized to detect a number of gasses simultaneously with a 3-sigma limit of detection (LOD) (e.g., 1 parts per billion (ppb)) for both narrow-line absorbing gas and broad-band absorbing gas.

The system 100 can include a laser 102 (e.g., single-mode near infrared laser, pump laser, etc.) that can be coupled to an amplifier 104 to amplify the output of the laser 102. The amplifier 104 can be coupled to an input of an optical frequency comb (OFC) 106. The OFC 106 can be a microresonator-based OFC with a narrow-line width radiation source available in the near-infrared spectrum (e.g., 1300 nanometers-2000 nanometers).

The OFC 106 can provide additional comb lines at a number of different wavelengths. The number of comb lines can be at wavelengths that are different than the output of the laser 102. In some embodiments, the OFC 106 can provide a number of comb lines within a wavelength range that can be utilized for detecting the number of different gasses within the cavity 110. In some embodiments, the cavity 110 can be a high finesse optical cavity such as a modified ring laser gyro block. The output of the OFC 106 can be coupled to the cavity 110 by a number of coupling optics 108 (e.g., ball lens, mirror/window lenses, etc.) that can alter a direction of the light output from the OFC 106, focus the light output from the OFC 106, and/or alter a wavelength of the light output from the OFC 106. The coupling optics 108 can alter the light output from the OFC 106 based on a configuration of the cavity 110 (e.g., actual path length of a number of mirrors 112-1, 112-2, 112-3, effective path length of the cavity 110, etc.).

The cavity 110 can comprise a number of mirrors 112-1, 112-2, 112-3. The number of mirrors 112-1, 112-2, 112-3 can have an actual path length of approximately six centimeters. That is, a measured distance from a first mirror 112-2, to a second mirror 112-1, and to a third mirror 112-3 can be approximately six centimeters (e.g., five centimeters, seven centimeters, a distance between five centimeters and seven centimeters, etc.). In some embodiments, the number of mirrors 112-1, 112-2, 112-3 can comprise a number of mirrors with a low loss over a wide spectral band of approximately half an octave, or greater. In addition, the number of mirrors 112-1, 112-2, 112-3 can comprise a number of mirrors with a low loss over 500 nanometers (nm) in the near infra-red spectrum.

The number of mirrors 112-1, 112-2, 112-3 that can receive the light output from the OFC 106 and reflect the light output from the OFC 106 between the number of mirrors 112-1, 112-2, 112-3 to increase an effective path length of the light output from the OFC 106. For example, the light output from the OFC 106 can be received when the light output from the OFC 106 passes through a first mirror 112-3. In this example, the light output from the OFC 106 can be reflected by a second mirror 112-1 to a third mirror 112-2. In this example, the light can be reflected a plurality of times between the number of mirrors 112-1, 112-2, 112-3 to provide an effective path length of the light output from the OFC 106 that is between 2 kilometers and 3 kilometers, dependent on the loss in the number of mirrors 112-1, 112-2, 112-3.

In some embodiments, at least one of the number of mirrors 112-1, 112-2, 112-3 can be coupled to a piezo-transducer 114 (e.g., actuator, actuator utilizing a piezo-transducer, etc.) that can alter a position 116 of the at least one of the number of mirrors 112-1, 112-2, 112-3. For example, a mirror 112-1 can be coupled to a piezo-transducer 114 that can alter the position 116 of the mirror 112-1. Altering the position 116 can alter the actual path length of the number of mirrors 112-1, 112-2, 112-3 and/or alter the effective path of the output light from the OFC 106 between the number of mirrors 112-1, 112-2, 112-3.

In some embodiments, altering the position 116 of at least one of the number of mirrors 112-1, 112-2, 112-3 can alter a wavelength of the comb lines from the light output of the OFC 106. For example, altering the position 116 of at least one of the number of mirrors 112-1, 112-2, 112-3 can alter the comb lines from the OFC 106 across a free spectral range (FSR) of 1500 nm. In another example, altering the position 116 of at least one of the number of mirrors 112-1, 112-2, 112-3 can alter the comb lines from the OFC 106 into a resonance of the cavity 110, which can provide comb lines that can be altered across the FSA.

In some embodiments, a few hundred comb lines can be generated across the FSR by altering at least one of the number of mirrors 112-1, 112-2, 112-3. Altering at least one of the number of mirrors 112-1, 112-2, 112-3 can bring each of the plurality of comb lines into a resonance with the cavity 110. By bringing each of the plurality of comb lines into a resonance with the cavity 110 can provide strong comb lines (e.g., comb lines that can be utilized to determine an absorption of unknown gases that absorb light in the near infrared) across the FSR.

Each of the plurality of comb lines from the OFC 106 can be altered by altering the position 116 of the mirror 112-1 via the piezo-transducer 114 to bring each of the plurality of comb lines into resonance with the cavity 110 and each of the plurality of comb lines in resonance with the cavity 110 can be sent to an array of detectors 118 via a grating 117. In some embodiments, the grating 117 can include a virtually imaged phased array (VIPA) grating that can show a relatively large angular-dispersion verses wavelength change. In some embodiments, the grating 117 can comprise a dispersive spectrometer. As used herein, the dispersive spectrometer can comprise a dispersive spectrometer that can generate spectra by optically dispersing the incoming radiation into its frequency or spectral components. Common dispersive elements can include prisms and gratings 116.

In one example, the position 116 can be adjusted to a first position to bring a first comb line at a first wavelength into resonance with the cavity 110 and the first comb line can interact with a gas within the cavity and be sent to the array of detectors 118 to determine an absorption of the gas at the first wavelength. In this example, the position 116 can be adjusted to a second position to bring a second comb line at a second wavelength into resonance with the cavity 110 and the second comb line can interact with the gas within the cavity 110 and be sent to the array of detectors 118 to determine an absorption of the gas at the second wavelength. In this example, the position 116 can be altered an additional plurality of times to bring each of a plurality of comb lines into resonance with the cavity 110 across a FSR. In some embodiments, the piezo-transducer 114 can adjust a mirror 112-1 at a distance of 7 nanometers/volt (nm/V).

In some embodiments, a first comb line at a first wavelength that is in resonance with the cavity 110 can be mapped to a unique pair of detectors within the array of detectors. In addition, a second com line at a second wavelength that is in resonance with the cavity 110 after a position 116 is altered can be mapped to a unique pair of detectors that are different than the unique pair of detectors associated with the first comb line at the first wavelength. In these embodiments, the pair of detectors can integrate a power in the comb lines while the comb line is in resonance with the cavity 110. Altering the position 116 to bring the plurality of comb lines into resonance with the cavity 110 and mapping each of the plurality of comb lines to a unique pair of detectors can provide a complete spectrum of a gas within the cavity 110 for each scan.

In some embodiments, the cavity 110 can be filled with an unknown gas. In some embodiments, there can be an additional cavity that is filled with a known gas and utilized with the cavity 110 to determine a composition of the unknown gas within the cavity 110. That is, the additional cavity can be utilized as a control to compare with the cavity 110 that is filled with an unknown gas.

By altering the position 116 of at least one of the number of mirrors 112-1, 112-2, 112-3 can provide a greater number of comb lines across the FSR range compared to previous systems and methods to ensure that a comb line will be closer to the absorption wavelength of the gas within the cavity 110.

Figure 2:
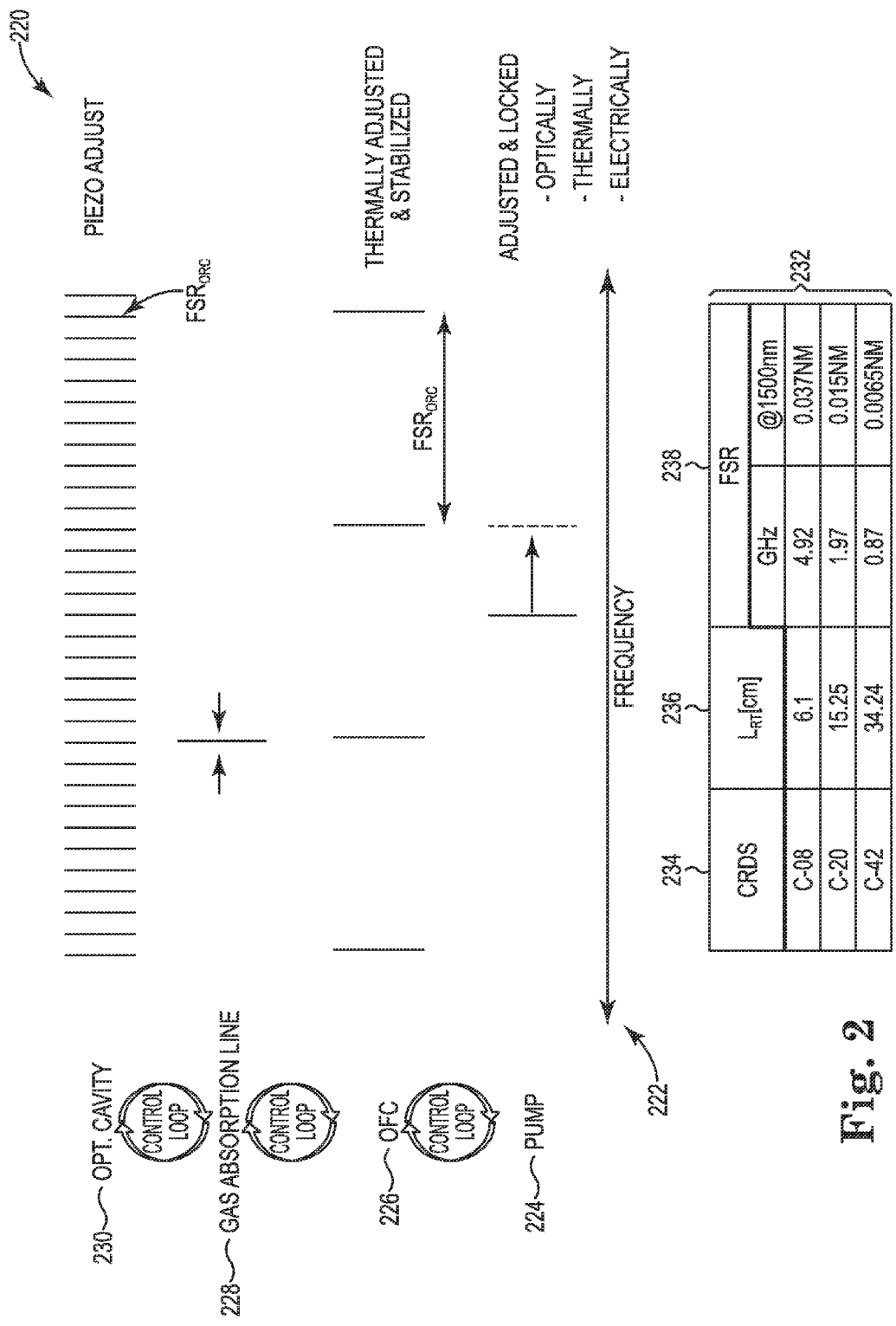
FIG. 2 is an example of a method for cavity-enhanced spectroscopy according to one or more embodiments of the present disclosure.

FIG. 2 is an example of a method 220 for cavity-enhanced spectroscopy according to one or more embodiments of the present disclosure. The method 220 can include a frequency range 222. In some embodiments, the frequency range 222 can include a range of wavelengths and/or frequencies in the near infrared region (e.g., 800 nanometers to 2500 nanometers). In some embodiments, the frequency range 222 can include a range of frequencies across the spectrum the ultraviolet (UV) region to the far infrared region.

A laser 224 (e.g., pump laser, etc.) can be utilized to generate a comb line at a particular frequency within the frequency range 222. In some embodiments, the laser 224 can be tuned (e.g., adjusted, etc.) via a tuner (e.g., thermal tuner, optical tuner, electrical tuner, etc.) that is coupled to the pump laser. The laser 224 can be tuned to a desired wavelength to be sent to an optical frequency comb (OFC) 226 that is coupled to the laser 224.

The OFC 226 can receive light at a tuned wavelength from the laser 224 to produce a number of comb lines that span the frequency range 222. There are four comb lines shown, but there can be more or fewer comb lines in certain embodiments. The number of comb lines can have a relatively large number of wavelengths between each of the number of comb lines. For example, the OFC 226 comb lines can span a particular distance (e.g., range of wavelengths) from a next closest comb line. The particular distance can be measured in a difference between the wavelength of a first comb line and the wavelength of a second comb line.

In some embodiments, the OFC 226 can be coupled to a tuner (e.g., thermal tuner, etc.) to alter a wavelength of the number of comb lines. In some embodiments, the tuner can alter the number of comb lines such that the comb lines extend over the frequency range 222. That is, the tuner can alter the comb lines from the OFC 226 to extend throughout the range of the infrared region (e.g., a number of comb lines near 800 nanometers and a number of comb lines near 2500 nanometers).

In some embodiments, the OFC 226 can be coupled to a cavity 230 (e.g., optical cavity, cavity 110 as referenced in FIG. 1, etc.). The cavity 230 can comprise a number of mirrors as described herein in reference to FIG. 1. The cavity 230 can include a known or unknown gas with a particular gas absorption line 228. In some embodiments, the cavity 230 can include a plurality of different gasses with a plurality of different corresponding absorption lines.

As described herein, the number of comb lines from the OFC 226 can be altered by the cavity 230 by altering at least one of the number of mirrors within the cavity 230 to bring the number of comb lines into resonance with the cavity 230. For example, the cavity 230 can receive the number of comb lines from the OFC 226 and generate a plurality of additional comb lines by altering the at least one of the number of mirrors so that the comb lines from the OFC 226 are brought into resonance with the cavity 230 to generate additional comb lines at the additional wavelengths. That is, the cavity 230 can be utilized to expand each of the comb lines from the OFC 226 into a plurality of additional comb lines by bringing each of the comb lines from the OFC 226 into a number of different resonances with the cavity 230 to generate additional comb lines.

FIG. 2 also includes a table 232. The table 232 includes a number of cavity ring-down spectroscopy (CRDS) devices 234 (e.g., C-08, C-20, C-42, etc.). Each of the CRDS devices 234 include a corresponding light round trip ($L_{RT}$) in centimeters (cm). In addition, each of the CRDS devices 234 include a corresponding free spectral range (FSR) with a gigahertz (GHz) value representing frequency and wavelength value at 1500 nanometers.

As shown in FIG. 2, there can be a plurality of comb lines from the cavity 230 between each of the comb lines from the OFC 226. By generating a number of additional comb lines between each of the comb lines from the OFC 226 the likelihood that a comb line from the cavity 230 will be generated at a wavelength that will be absorbed by the gas within the cavity can be increased. For example, a gas can have an absorption line 228 that is between a first comb line from the OFC 226 and a second comb line from the OFC 226. In this example, it might not be possible to correctly identify the gas since the comb line may not be close enough to the absorption line of the gas.

Figure 3:
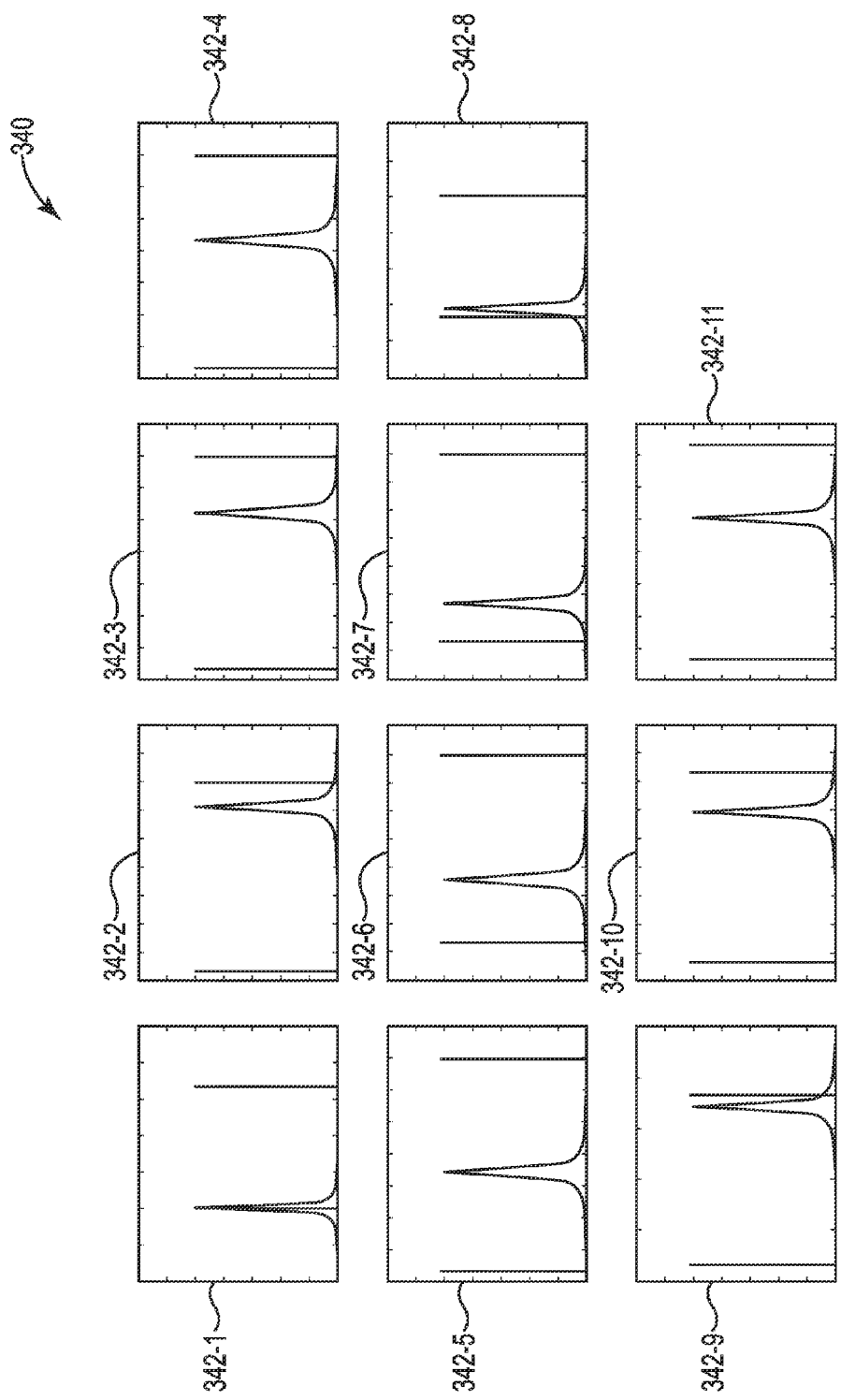
FIG. 3 is an example of a graphical representation corresponding to cavity-enhanced spectroscopy according to one or more embodiments of the present disclosure.

FIG. 3 is an example of a graphical representation 340 corresponding to cavity-enhanced spectroscopy according to one or more embodiments of the present disclosure. The graphical representation 340 can include a plurality of absorption spectra graphs 342-1, 342-2, . . . , 342-N for each of the plurality of comb lines from a cavity-enhanced spectroscopy system as described herein. As described herein, the cavity-enhanced spectroscopy system (e.g., system 100 as referenced in FIG. 1) can include a laser coupled to an optical frequency comb that is coupled to a cavity.

The plurality of absorption spectra graphs 342-1, 342-2, . . . , 342-N can each include a comb line from the cavity and a line representing the frequency of the laser coupled to the OFC. In a number of the absorption spectra graphs 342-1, 342-2, . . . , 342-N the comb line from the cavity and/or the line from the laser can be closer to an absorption peak of the gas. In some embodiments, a portion of the number of absorption spectra graphs 342-1, 342-2, . . . , 342-N can be selected based on how close the comb line and/or the laser line is to the absorption peak. For example, absorption spectra graph 342-1, absorption spectra graph 342-8, and absorption spectra graph 342-9 can be selected. In this example, the selected absorption spectra graphs (e.g., absorption spectra graph 342-1, absorption spectra graph 342-8, and absorption spectra graph 342-9) can be selected over the remaining absorption spectra graphs 342-1, 342-2, . . . , 342-N since the selected absorption spectra graphs represent comb lines that are relatively closer to the absorption peak.

As described herein, a "module" can include computer readable instructions that can be executed by a processing resource to perform a particular function. A module can also include hardware, firmware, and/or logic that can perform a particular function.

As used herein, "logic" is an alternative or additional processing resource to execute the actions and/or functions, described herein, which includes hardware (e.g., various forms of transistor logic, application specific integrated circuits (ASICs)), as opposed to computer executable instructions (e.g., software, firmware) stored in memory and executable by a processing resource.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above elements and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A system for cavity-enhanced spectroscopy, comprising:
   an optical frequency comb (OFC) coupled to a laser source to provide a first comb line and a second comb line; and
   a cavity coupled to the OFC comprising a number of mirrors to receive the first comb line and the second comb line, wherein at least one of the number of mirrors is coupled to a piezo-transducer configured to alter a position of the at least one of the number of mirrors to bring the first comb line into resonance with the cavity and alter the position of the at least one of the number of mirrors to bring the second comb line into resonance with the cavity.

2. The system of claim 1, wherein the number of mirrors comprise a number of mirrors with a low loss over a wide spectral band of at least half an octave.

3. The system of claim 1, wherein the number of mirrors comprise a number of mirrors with a low loss over 500 nanometers (nm) in the near infra-red spectrum.

4. The system of claim 1, wherein the at least one of the mirrors coupled to the piezo-transducer is altered to bring a comb line from the OFC into resonance with the cavity.

5. The system of claim 1, wherein the effective path of the cavity is between 2 kilometers and 3 kilometers.

6. The system of claim 1, comprising a dispersive spectrometer that is coupled to the cavity.

7. A system for cavity-enhanced spectroscopy, comprising:
   an input of an optical frequency comb (OFC) coupled to a laser source to provide a first comb line and a second comb line;
   a cavity coupled to an output of the OFC comprising at least three low loss mirrors to receive the first comb line and the second comb line, wherein at least one of the low loss mirrors is coupled to a piezo-transducer configured to
      alter a position of a comb line that is one of the first comb line and the second comb line from the output of the OFC; and
      bring the first comb line into resonance with the cavity and alter the position of the at least three low loss mirrors to bring the second comb line into resonance with the cavity; and
   a dispersive spectrometer coupled to an output of the cavity.

8. The system of claim 7, wherein the position of the comb line is altered through a free spectral range (FSR) of 1500 nm.

9. The system of claim 7, wherein the cavity comprises a six centimeter (cm) physical path length.

10. The system of claim 7, wherein the cavity provides a 1.5 kilometer effective path length.

11. The system of claim 7, wherein the at least three low loss mirrors are positioned to reflect the output of the OFC to at least one of the other at least three low loss mirrors.

12. The system of claim 7, wherein the cavity comprises an unknown gas.

13. The system of claim 7, comprising a reference cavity that comprises a known gas.

14. The system of claim 13, wherein an absorption spectrum of the cavity is compared to an absorption spectrum of the reference cavity.

15. A method for cavity-enhanced spectroscopy, comprising:
   receiving output light from an optical frequency comb (OFC) coupled to a laser source at an input of a cavity comprising a number of mirrors, wherein the OFC provides a first comb line and a second comb line to the input of the cavity;
   adjusting, utilizing a piezo-transducer, at least one of the number of mirrors to alter the first comb line of the received output light to bring the first comb line into resonance with the cavity;
   adjusting, utilizing the piezo-transducer, at least one of the number of mirrors to alter the second comb line of the received output light to bring the second comb line into resonance with the cavity;
   reflecting, utilizing the number of mirrors, the received output light onto at least one other mirror from the number of mirrors; and
   providing the reflected light to a detector array that is coupled to the cavity.

16. The method of claim 15, wherein providing the reflected light to a detector array comprises providing light from the cavity to the detector array and providing light from a reference cavity comprising a known gas.

17. The method of claim 15, wherein reflecting the received output light includes reflecting, utilizing the number of mirrors, the received output light onto each of the number of mirrors to extend an effective path of the output light.

18. The method of claim 15, comprising generating a graphical representation of an absorption spectrum for an unknown gas within the cavity.

19. The method of claim 15, wherein adjusting, utilizing the piezo-transducer, at least one of the number of mirrors to alter the comb line includes altering the comb line across a free spectral range (FSR) of 1500 nm.

20. The method of claim 15, wherein the number of mirrors provide an actual path length of six centimeters (cm).

* * * * *